United States Patent [19]

Chu

[11] Patent Number: 4,493,793

[45] Date of Patent: Jan. 15, 1985

[54] SOLUBLE IMMUNOASSAY REAGENT COMPRISING LECTIN COVALENTLY BONDED TO REACTIVE COMPONENT

[75] Inventor: Albert E. Chu, San Mateo, Calif.

[73] Assignee: E-Y Laboratories, San Mateo, Calif.

[21] Appl. No.: 292,739

[22] Filed: Aug. 14, 1981

Related U.S. Application Data

[62] Division of Ser. No. 972,921, Dec. 26, 1978, Pat. No. 4,371,515.

[51] Int. Cl.$^3$ .................. C07G 7/00; G01N 33/48; G01N 33/54; G01N 33/68; G01N 33/78; A61K 39/29; A61K 39/106; A61K 35/78

[52] U.S. Cl. .................. 260/112 R; 260/112.5 R; 424/11; 424/85; 424/88; 424/177; 424/195; 436/500; 436/501; 436/503; 436/528; 436/529; 436/827; 435/7

[58] Field of Search .............. 424/1, 8, 11, 85, 88, 424/177, 195, 12; 23/230 B; 260/112 B, 112 R, 112.5; 435/7; 436/500, 501, 503, 528, 529, 536, 827

[56] References Cited

U.S. PATENT DOCUMENTS

3,994,870 11/1976 Neurath .................. 424/86 X
4,041,146  8/1977 Glaever .................. 424/7 X
4,289,747  9/1981 Chu .

OTHER PUBLICATIONS

Miles Biochemicals/Miles Res. Products, Miles Labs, 1976, pp. 106–108.
Nicolson, Nature, N.B. vol. 239, Oct. 18, 1972, pp. 193–197.
Lis et al., Ann Rev. Biochem., vol. 42, 1973, pp. 541–551, 558–574.
Miles Res Products, Quality Line Bulletin, Summer, 1978, Miles Labs, Elkhart, Ind., pp. 3–4.
Aspberg et al., Acta Chem. Scand., vol. 24, 1970, pp. 1839–1840.
Avigad, Analytical Biochem., vol. 86, 1978, pp. 443–449.
Gonatas, Chem. Abs., vol. 80, 1974, Ab. No. 12154t.
Smith, Chem. Abs., vol. 74, 1971, Ab. No. 40239u.

Primary Examiner—Anna P. Fagelson
Attorney, Agent, or Firm—Flehr, Hohbach, Test, Albritton & Herbert

[57] ABSTRACT

A lectin is covalently bonded to an immunological conjugate such as an antibody-antigen or its equivalent. Then, the lectin-conjugate is isolated from the reaction product mixture by one of a number of alternative techniques involving one or more of the following types of reaction; (1) reversible reaction of the lectin with an insolubilized sugar to isolate lectin from the remainder of the mixture, (2) reaction of one immunological component (e.g., antibody) bonded to the lectin with an insolubilized corresponding component (e.g., antigen) to separate the antibody components from the remainder of the reaction mixture, and (3) filtration of the reaction components to separate on the basis of product molecular weight, size and/or shape of the components.

5 Claims, No Drawings

SOLUBLE IMMUNOASSAY REAGENT COMPRISING LECTIN COVALENTLY BONDED TO REACTIVE COMPONENT

This is a division of application Ser. No. 972,921 filed Dec. 26, 1978, now U.S. Pat. No. 4,371,515.

The present invention relates to the formation and isolation of a lectin bonded to one component of immunological conjugate (e.g., antigen or antibody), particularly for use in immunoassays.

Common immunoassay techniques include the so-called sandwich or competitive binding techniques. Such techniques typically employ various immunological reactions with labelled antibody or antigen. A common problem in such techniques is the separation of the bound labelled antigen or antibody from the remainder of the reaction mixture containing unbound labelled material. The disadvantages of the various known techniques for accomplishing this objective are set out in my copending patent application entitled "Immunological Determination Using Lectin" filed simultaneously herewith (herein referred to as my copending patent application).

Lectins are known to include receptor sites or lectin reactive sites of high specificity for a particular sugar or sugars but not for other ones. The bond formed between the lectin and sugar are known to be reversible. The potential advantage of using this type of reaction for separation in an immunoassay has not been disclosed in the prior art. Instead, the lectin-sugar reaction has been used in a limited manner as a biological assay tool. For example, lectin coupled with an enzyme has been employed to selectiviely label glycoprotein in a biologically derived cell, followed by determination of the enzyme label as a measure of the glycoprotein.

In accordance with the invention, lectin and one component of an immunological conjugate are firmly bonded to each other, preferably through covalent bonds, and the product is isolated from its reactiom mixture, herein designated the "coupling reaction mixture", for use in a subsequent immunoassay. Such conjugate includes antigen, antibody or portions and equivalents thereof. (For simplicity of description, unless otherwise specified, antigen will be designated as the one component of an immunological conjugate bound to the lectin and the bound product will be designated the "lectin-antibody product". In general, the use of a hyphen ("-") between moieties refers to a bond.)

A major advantage of this lectin-antibody product is its ability for reversible attachment to a sugar specifically reactive with it on a solid surface for separation from a reaction mixture. Then, it is releasable by directing a solution of the same type of sugar past the solid surface. This eliminates the disadvantages of cleaving immunological bonds.

Various techniques may be employed to isolate the lectin-antibody product from the coupling reaction mixture. In a first isolation method, the free and bound antibody in the coupling reaction mixture are reacted with insolubilized antigen. Then, the remainder of the mixture, containing free lectin, is removed. Thereafter, the antigen-antibody bond is broken and the soluble portion of the reaction mixture is reacted with a volume of insolubilized sugar. The soluble portion, containing antibody unbound to lectin, is removed. Then the insolubilized sugar is washed with soluble sugar to form a solution containing the isolated lectin-antibody solution. In an alternative or second isolation method, the order of the steps relating to the antigen-antibody reaction and to the lectin-sugar reaction may be reversed.

In a third isolation method, the coupling reaction mixture is passed through a filtration bed to separate the lectin-antibody product from free lectin and free antibody as a function of time on the basis of the respective molecular weights of the materials. Then, the lectin-antibody is separated as a fraction from the remainder of the reaction mixture.

In a fourth alternative method features of the second and third alternative methods are employed. Namely, the coupling reaction product is reacted with insolubilized sugar to bind selective lectins, and antibody unbound to lectin is removed from the insolubilized product. Then, the lectin bound product is released by contact with insolubilized sugar and passed through a filtration bed which separates the free lectin and lectin-antibody product on the basis of molecular weight. Thereafter, the lectin-antibody fraction is isolated.

It is an object of the invention to provide an isolated lectin-immunological conjugate product, particularly for use in an improved immunoassay technique.

It is a specific object of the invention to provide an isolated lectin-immunological conjugate of the foregoing type suitable for use in separating a labelled immunological reaction product from the remainder of its reaction mixture by reversible bonding on a solid surface containing sugar and thereafter by releasing it into solution for label measurement.

Further objects and features of the invention will be apparent from the following description in which the preferred embodiments are set forth in detail.

The lectin-immunological conjugate of the present invention is useful for determining the correspondingg immunological component of the conjugate pair. In other words, the term conjugate includes one component of any pair of substances which immunologically bind to each other. Specifically, conjugate pairs include antigens and their antibodies, biologically functional haptens and their antibodies, enzymes and their substrates, hormones and their receptors, and vitamins and their receptors. The conjugate components herein may be broadly considered as an antigen-antibody or portions and equivalents of the same. As set out above, for simplicity of description, unless otherwise specified, the immunological conjugate bound to the lectin herein will be designated as antibody. The isolated lectin-antibody product is particularly useful for measuring antigen as the component of a fluid sample, specifically, blood serum.

Lectins are proteins or glycoproteins that have receptor site specificity for a particular sugar or sugars but not for other sugars. For example, Concanvalian A (Con A) has a specificity for alpha-D-glucose and alpha-D-mannose. When a ligand such as glucose is linked convalently to a solid matrix, Con A will be retained on the surface because a glucose ligand will have avidity with Con A's receptor site. This bond is reversible. Thus, a solution of glucose will release the Con A from the surface.

In the present system, the lectin is irreversibly bonded to the immunological conjugate, specified as antibody herein, by known covalent bonding techniques. Such binding is suitably performed by cross-linking the lectin with antigen or antibody through a bifunctional cross-linking agent. Suitable bifunctional compounds are found in *Review* by Peters, K. and Richards, F. M., (Ann. Rev. Biochim. 46 (1977) 523). Alkyl imidates show a high degree of specificity among the functional groups presented to them by a protein. The reaction is specific for primary amino groups. Specific disclosed coupling reagents include amidoesters such as dimethyl malonimidate, azides such as the acryl azide of tartryl diazide which reacts readily with amino groups to produce amidelinkages, aryl dihalides (e.g., 1,5-difluoro-2,4-dinitrobenzene, or 4,4'-difluoro-3,3'-dinitrophenyl sulfone), glutaraldehyde, dimaleimide, mixed anhydride, mixed aromatic or aliphatic dicarboxyl, N-hydroxysuccimide ester, and other known cross-linking agents. Catalytic reagents such as 1-ethyl-3(3-dimethylamino proply)carbodiimide hydrochloride may be used to form covalent bonds between amino groups of one molecule to carboxyl groups of another.

All of the foregoing bonds are essentially irreversible. In addition, bifunctional reagents with functional groups such as disulfide or glycol may be used. Such bonds can be broken after the cross-linking reaction. Such reagents include dimethyl 3,3'-dithiobispropionimidate, succinimidyl propionimidate, N-(3-Fluooro-4,6-di(nitrophenyl)-cystamine, tartryl diazide, tartryl di(glycylazide) and tartryl di($\epsilon$-amino caproylazide).

The lectin-antibody product in isolated form is useful in a variety of immunoassay techniques set out in detail in my copending patent application. Such immunoassay techniques include homogenous or flowthrough competitive systems and homogeneous or flowthrough sandwich systems, and are particularly useful for the determination of multiple antigens or antibodies in an immunological sample. The details of such various methods are set forth in my aforementioned patent application, incorporated at this point by reference.

The reversible sugar-lectin bond provides the mode of separating the reaction product in each of the immunoassay techniques set forth in the previous paragraph. The highly specific nature of the sugar-lectin bond renders the system particularly versatile. A sample list of lectins and specific sugars are set out below.

TABLE I

| Lectin | Sugar |
| --- | --- |
| Arachis Hypogaea Agglutinin (PNA) | D-Gal$\beta$(1 → 3)-GalNAc |
| Bauhinia Purpurea Agglutinin (BPA) | D-GalNAc, D-Gal |
| Bendeirea Simplicifolia Agglutinin (BSA) | $\alpha$-D-Gal |
| Canavalia Ensorform's Agglutinin (CON A) | $\alpha$-D-Man, $\alpha$-D-Glc. |
| Dolichos Biflorus Agglutini (DBA) | $\alpha$-D-GalNAc |
| Glycine Max (SBA) | D-Gal, $\alpha$-D-GalNAc |
| Lens Culinaris (LcH) | $\alpha$-D-Man, $\alpha$-D-Glc |
| Limulus Polyhemus (LPA) | Sialic Acid |
| Lotus Tetragonolobus (Lotus A) | $\alpha$-L-Fucose |
| Phaseolus Vulgaris (L-PHA) | D-GalNAc |
| Phaseolus Limensis (LBA I) | $\alpha$-D-GalNAc |
| Phaseolus Vulgaris (H-PHA) | D-GalNAc |
| Pisum Sativum (PEA) | $\alpha$-D-Man, $\alpha$-D-Glc. |
| Phytolacca Americana (Pokeweed) | |
| Ricinus Communis (RCA I) | $\beta$-D-Gal |
| Ricinus Comunis (RCA II) | $\beta$-D-Gal, D-GalNAc |
| Sophora Japonica (SJA) | $\alpha$-D-GalNAc |
| Triticum Vulgaris (WGA) | ($\beta$(1 → 4)-D-GlcNAc)2 (Sialic Acid) |
| Ulex Europeus (UEA I) | $\alpha$-L-Fucose |
| Ulex Europaeus (UEA II) | (D-GlacNAc)2 |
| Wisteria Floribunda (WFA) | D-GalNAc |

It should be understood that isomers of the foregoing lectins may also be employed in accordance with the scope of the present invention. The above sugars are the ones with highest affinity for the lectin. Each lectin may bind to other sugars with less affinity.

The foregoing lectins are firmly bound to the appropriate immunological substance, e.g., antigen, antibody or equivalent bifunctional reagents as set out above. Thus, any of the substances which form immunological conjugates may be employed in the lectin-immunological substance pair.

Exemplary antigens which would be used to test the corresponding antibody in a system are as follows:

TABLE II

Albumin
Carcinoembryonic antigen
Choriogonadotropin
Haptoglobin
Hepatitis B surface antigen
IgE
IgG
IgM
Insulin
Placental Lactogen
Pregnancy-associated macroglobulin
Vibrio Cholerae-exotoxin lipopolysaccharide Exemplary haptens are as follows:

TABLE III

Cortisol
Estrogens
2,4-Dinitrophenol
Progesterone
1 Thyrotropin
Morphine & other opiates
Amphetamine
Barbituate
Methadone
Benzoyl ecogonine (Cocaine metabolite)
Diphenylhydantoin
Phenobarbital
Primidone
Digoxin
Morphine and Codeine
Thyroxine By way of example, antibodies against the antigens in the following table may be employed.

TABLE IV

Amoeba, strain HK-g
Albumin, serum
Allergens, various
Carcinoembryonic antigen
choriogonadotropin
DNA
human IgG, IgM, IgA
Dextran
2,4-dimtrophenol
Echinococcus granulous
E. Coli enterotoxin o and kl antigens
$\alpha$-Fetoprotein
YGlobulin
IgG myeloma proteins
Immunologlobulin light chains
Hog cholera virus
Onchocera volualus
Plosmodium species
Rubella Virus Salmonella species, O antigens
Schistosoma mansoni
Streptolysin O
Toxoplasma Condiu
Trichinella spiralis
Trypanosoma Cruzi
Trypanosoma rhodescenes and Trypanosoma Brucei
Vibrio cholerae, exotoxin and liposaccharide In essence, the present method may be referred to as a first stage (in which the lectin and conjugate component, specifically antibody, are covalently bonded) and a second (isolation) stage. The reaction product of the first stage includes unreacted reactants (lectin, antibody, and cross-linking agent), the desired lectin-antibody reaction product, and possibly other products linked by the highly reactive cross-linking agent such as antibody-antibody, lectin-lectin, or even multiple lectins attached to a single antibody or multiple antibodies attached to a single lectin. As set out above, this composite reaction product is referred to herein as the coupling reaction mixture. The main difference among the various techniques set out in the present application is with respect to the second or isolation stage.

FIRST ISOLATION METHOD

In this method, the coupling reaction mixture is first mixed with antigen in insolubilized form. Such antigen is selectively immunologically reactive with the antibody of the lectin-antibody product to be isolated. A large excess of the insolubilized antigen is present, and so essentially all of the free antibody and antibody-lectin products react with and are retained by the insolubilized antibody. This step is referred to herein as the immunological reaction step.

In a preferred form of this immunological reaction step, the insoluble antigen is formed by covalent bonding to a solid surface by techniques similar to those employed for covalent bonding of the lectin and antibody.

The immunological reaction may be performed by incubating the antigen and antibody in a vessel in a batch reaction. However, where possible, it is preferable to increase the rate of production by flowing reaction mixture continuously through a contained volume of insolubilized antigen in a vacuum bed or for retention of the antibody in the bed. For such a flowthrough application, it is preferable that the solid phase to which the antigen is covalently bonded be of a porous character which permits free passage of solutions. Thus, for example, the antigen can be covalently bonded to a cellulose filter paper bed. Also, particulate beads may be employed to provide less resistance to flow. Such beads may be formed of glass, polystyrene, sheet polyacrylamide gel, nylon-6, agarose, or other material capable of forming a covalent bond with the antigen.

After the above immunological reaction, the insolubilized antigen-antibody product is separated from the remainder of the fluid reaction mixture which contains other reaction products including free lectin. Preferably, this separation step is performed by retention of the antibody and antibody-lectin on a column of the insolubilized antigen while permitting the remainder of the reaction mixture to pass to waste.

After the above separation, the immunological bonds may be broken by conventional means such as the use of a mildly acidic (e.g., 0.1M acetic acid) or basic (e.g., 3M urea) solution. Suitable pH ranges for this purpose are on the order of 1 to 3 and 11 to 13. After breaking the bonds and separation from the column, the product is neutralized to avoid adverse effects on the reactivity of the antibody.

After the immunological bonds are broken, the insolubilized antigen may be reused, if desired, for a subsequent batch of lectin-antigen product to be isolated. In other words, in this step, the insolubilized antigen is regenerated.

The soluble portion removed from the foregoing column has been cleansed of lectin but still may include free antibody or antibody-antibody pairs. To remove these impurities, the solution of the previous step is contacted with insolubilized sugar moieties selectively and reversibly reactive with the specific lectin to permit the sugar to react with the lectin of the lectin-antibody product. That portion of the mixture which does not react with the insolubilized sugar, containing antibody unbound to lectin, may be permitted to pass to waste. In this manner, the lectin-antibody product has been isolated.

The above reaction with insolubilized sugar is preferably performed by flow through a porous bed of insolubilized sugar. The same form of bed as set out with respect to the antibody may be employed. The sugar is preferably covalently bonded to the substrate by the foregoing known techniques. Suitable substrates for the sugar include acid treated agarose beads, such as of a type sold under the trademark Sepharose, or galactosamine linked agarose beads.

Although the foregoing insolubilized sugar-lectin-antibody may have some limited immunoassay application, it is preferable to isolate the lectin-antibody product in soluble form. This is readily accomplished by passing a solution of sugar of the same type as the insolubilized sugar moieties through a contained volume of it. This causes the lectin-antibody to be washed from the insolubilized sugar by conversion into a solubilized form. Then, the soluble lectin-antibody is separated. The sugar and excess cross-linking agent is readily removed from the lectin-antibody product by conventional isolation techniques such as dialysis or by passage through a gel filtration column as of the type sold under the Sephadex G25 trademark.

The bifunctional coupling agents employed to couple the lectin and antibody are highly reactive. Accordingly, in certain cases, it is possible that the coupling agent would block the sites of the lectin which are reactive with sugar. This blocking action could cause the lectin-antibody to flow through the insolubilized sugar column without retention, leading to a potential significant loss of product.

To minimize this potential loss of product, it is preferable to include a source of sugar in the lectin-antibody coupling reaction which is selectively and reversibly reactive with the lectin. This sugar blocks the sugar reactive sites during coupling. After completion of the coupling reaction, the sugar is removed from the sugar-reactive sites of the lectin, suitably by dialysis. Thereafter, the sugar reactive lectin is reacted with the insolubilized sugar as set out in the above isolation step. It is possible that multiple lectins may be bound to a single antibody or that multiple antibodies may be bound to a single lectin during the coupling reaction. It it is desired to produce an exceptionally high purity product of only one lectin bonded to one antibody, it is possible to further isolate the reaction mixture by filtration. That is, the product from the foregoing isolation procedure may be passed through a filtration bed capable of separating components in the stream as a function of time on the basis of their respective molecular weights, size and/or shape. Thus, for example, the lectin may have a molecular weight on the order of 110,000 and an antibody on the order of 160,000. By separation of a fraction on the order of 270,000 or less, lectin-antibody products including multiple antibody or lectin are separated from the single lectin-antibody product. This is suitably performed by gel filtration through a molecular sieve or the like by known techniques.

SECOND ISOLATION METHOD

This method is an alternative to the first isolation method. Specifically, in a first step, the coupling reaction product is contacted with insolubilized sugar moieties selectively and reversibly reactive with the lectin in the mixture to cause reversible binding therebetween. Thus, the insolubilized sugar reacts with the free lectin and with the lectin-antibody product. The remainder of the reaction mixture containing unreacted antibody and coupling reagent is separated as a soluble product stream from the insolubilized sugar. The form of the sugar and the separation technique (e.g., passing of the product through a bed of the insolubilized sugar) are the same as that set forth with respect to the analogous step in the first method.

As with the first method, it is preferable to protect or block the sugar reactive sites of the lectin during the coupling reaction to avoid excessive loss of lectin-antibody product which could otherwise by-pass the insolubilized sugar without retention. In this procedure, the sugar present at such reactive sites is removed therefrom prior to contact with the insolubilized sugar. As with the first method, this is preferably accomplished by dialyzing of the sugar.

In the next step, the free lectin and lectin-antibody bound to the insolubilized sugar is washed from the solid surface by passage of a soluble sugar of the same type as the insolubilized sugar causing the lectin to be converted to a solubilized form.

This soluble sugar product is then contacted with insoluble antigen specifically immunologically reactive with the antibody of the lectin-antibody product. Then, an immunological reaction is permitted to occur. This is analogous to the immunological reaction of the foregoing method. The remainder of the reaction mixture containing lectin unbound to antibody is then removed from the product.

In the next step, the insolubilized antigen-antibody-lectin product is subjected to conditions to break the immunological bond between the antigen and antibody. Suitable conditions are set out above. Then, the lectin-antibody is removed.

In essence, the second method is the homologue of the first one with a reversal of the order of immunological reaction and insolubilized sugar-lectin binding steps.

THIRD ISOLATION METHOD

In this method, the reaction product from coupling of the lectin-antibody is isolated in a highly simplified manner in comparison to the foregoing ones.

The reaction mixture from lectin-antibody coupling is subjected to a separation treatment based solely upon molecular weight. As set out above, a typical lectin may have a molecular weight of 110,000 while a typical antibody has a molecular weight of 160,000. Thus, the desired lectin-antibody product has a molecular weight of 270,000 a lectin-lectin product of 220,000 and an antibody-antibody product of 320,000, while multiple combinations of lectin and antibody have a higher molecular weight. Thus, the product may be passed through a filtration bed in which the components of the mixture in the stream are separated as a function of time on the basis of their molecular weights. Thereafter, the fraction of the stream corresponding to the desired molecular weight, in this instance 270,000, is collected to the exclusion of the remainder of the reaction mixture.

Conventional filtration beds may be employed for separation by molecular weight to accomplish this isolation technique. For example, the product may be passed through a gel filtration bed of the type sold under the trademark Sephadex 200. In addition, other molecular sieve type beds may be employed.

For better isolation, the above filtration technique may be supplemented by a subsequent isolation step as follows. The lectin-antibody fraction may be contacted with a column of insolubilized sugar selectively and reversibly reactive with the lectin. In this manner, insolubilized sugar and lectin of the lectin-antibody are reversibly bound. The remainder of the mixture is permitted to pass through the column. The lectin of the lectin-antibody bound to the column necessarily includes a sugar-reactive site. Thus, this step removes as a soluble fraction all lectin-antibody in which the lectin includes a reactive site. This is important when the lectin-antibody is to be used in subsequent immunoassay techniques.

As set out above, it is preferable that the lectin-antibody be in a soluble form. The lectin-antibody is removed from the insolublized sugar in the last named step by passage of a sugar solution through the column and removing the lectin-antibody in soluble form. Thereafter, the soluble sugar is removed from the lectin-antibody, as by dialysis.

FOURTH ISOLATION METHOD

This method is a variant of the second method in which the reaction product from coupling of the lectin-antibody is first treated in the insolubilized sugar-lectin binding step as set forth above. Then, the free lectin and lectin-antibody bound to the column is washed from the column in a sugar solution also as set forth above.

The major difference of this method is that instead of the immunological reaction step, filtration is employed to remove free lectin and lectin byproducts. That is, the product washed from the insolubilized sugar column is passed through a filtration bed to separate the free lectin from the lectin-antibody product in the stream as a function of time on the basis of the difference in molecular weights of these two products. Then, the lectin-antibody is separated from the remainder of the reaction mixture. The foregoing conventional techniques from accomplishing this filtration separation may be employed with an appropriate variation in the sensitivity of the filtration medium to the differences in molecular weight.

The product formed by the foregoing process is an isolated soluble reaction product of a lectin bonded to one component of an immunological conjugate. In the foregoing description, such one component is an antibody. However, other immunological materials may be substituted such as antigen, antibody, and portions and equivalents as set out above.

The foregoing lectin product finds particular application in immunoassay techniques in that it possesses the unique capability of highly specific and reversible binding with one or more sugars. To perform this function, the lectin must include at least one reactive receptor site which is specific for the sugar. Thus, precautions are set out above for assuring that such reactive sites are present.

When referred to the lectin-antibody product of the present invention, the term "isolated" means the product functionally isolated from significant interference from free lectin or antibody. Thus, in general, it may include a very minor percent of free lectin or antibody such as on the order of less than 1–5% depending upon the requirements of the particular immunoassay end use. Thus, purity of the product may be tailored to the requirements of the end use. If extremely high purity is required, the more detailed procedures set out above may be employed.

A further disclosure of the nature of the present invention is provided by the following specific examples of the practice of the invention to form the isolated lectin-antibody product. It should be understood that the data disclosed serve only as examples and are not intended to limit the scope of the invention. The formed products may be employed in immunoassay techniques disclosed in my copending patent application, the examples of which are incorporated at this point by reference.

EXAMPLE 1

5 mg. of purified PNA (lectin) is dissolved in 1 ml of buffer solution containing 0.1M lactose, 0.1M phosphate buffer pH 7.2, 0.15M sodium chloride, and 5 mg of goat anit-human IgG antibodies, and 10–20 microliter of a coupling agent (redistilled glutaraldehyde) is added. This mixture is incubated for one hour at room temperature. Dialysis against 1 liter 0.1M phosphate buffered saline. Then it is passed through a galactose (1→3) N-acetyl galactosamine linked agarose beads column having specificity to retain PNA and PNA-antibodies on the column matrix. The column is washed until the $OD^{280}$ measurement is 0.050. Then, the PNA complex is eluted from the column by using a specific sugar such as 0.5M lactose solution and then passed through a second column containing human IgG coupled agarose beads. The PNA-antibodies are dissociated from the matrix by using either 0.1M acetic acid. (Or 3M sodium isothiocyanate or other reagents.) The complex is extensively dialyzed against phosphate buffer saline. The eluted solution is concentrated and passed through a (Sephadex G200 type) gel filtration column which separates constituents by molecular weight, size and/or shape. (The fraction is collected which corresponds to a molecular weight of a lectin-antibody pair in a one to one conjugation ratio.)

EXAMPLE 2

To one ml of phosphate buffer saline pH 7.2 containing one mg PNA mixed with two ml of galactose (1→3) N-acetyl galactosamine or lactose linked agarose beads matrix specific for PNA binding. Glutaraldehyde is added and the mixture is incubated for 1–6 hours. The gel is washed on a sintered glass filter funnel with PBS. This gel is suspended in a solution of 1 mg of goat anti-human IgG antibodies overnight. The beads are washed with PBS and then washed with 0.1M specific sugar solution to release lectin-antibody complexes from the matrix. The eluant is collected and passed through a column containing human IgG coupled agarose beads. The rest of the procedure is the same as for Example 1.

EXAMPLE 3

5 mg lyophilized powder of PNA, 5 mg immunoglobulin fraction of rabbit anti-digoxin antisera and 5 mg purified D-galactose or lactose are dissolved in one ml of 0.1M phosphate buffer saline pH 7.2. To this mixture, one to five micromillimeter of 50% glutaraldehyde is added. This mixture is incubated at room temperature for one hour and applied to a column containing acid treated agarose beads or 2-amino-2-deoxygalactopyranoside covalently linked agarose beads. (Nearly all PNA and PNA-antibody will be retained on the solid matrix in the column.) A 0.2M galactose or lactose solution is added to this column. The single peak containing the PNA and the conjugates will appear from the eluent. This fraction is concentrated to 0.5 ml and passed through to a column $0.1 \times 100$ cm containing Sephadex G200. At the PNA-antibody combined molecular weight is over 200,000, the unreacted PNA is separated from the PNA-antibody conjugates. Condition for purification can be enlarged proportionally when a large preparation is necessary.

What is claimed is:

1. A soluble immunoassay reagent reaction product comprising a lectin covalently bonded to one reactive component capable of reacting with a corresponding component to form an immunological conjugate pair, said lectin including at least one free reactive receptor site having specificity for at least one type of sugar, said reactive component being selected from the group consisting of antigens, antibodies, and biologically reactive haptens, said antigens being selected from the group consisting of albumin, carcinoembryonic antigen, choriogonadotropin, haptoglobin, hepatits B surface antigen, IgE, IgG, IgM, insulin, placental lactogen, pregnancy-associated macroglobulin, and vibris cholerae-exotoxin lipopolysaccharide; said biologically reactive haptens being selected from the group consisting of cortisol, estrogens, progesterone, 1 thyrotropin, opiates, amphetamine, barbituate, methadone, benzoyl ecogonine (cocaine metabolite), diphenylhydantoin, primidone, digoxin, and thyroxine.

2. The reaction product of claim 1 in which said reactive component is an antibody.

3. The reaction product of claim 1 in which said reactive component is an antigen.

4. The reaction product of claim 1 in which said reactive component is a biologically reactive hepten.

5. The reagent of claim 1, wherein the biologically reactive hapten is phenobarbital, morphine or codeine.

* * * * *